United States Patent [19]

Abe et al.

[11] 4,423,032

[45] Dec. 27, 1983

[54] HAIR TREATMENTS

[75] Inventors: Yoshiaki Abe, Tokyo; Rikio Tsushima, Wakayama, both of Japan

[73] Assignee: Kao Soap Co., Ltd., Tokyo, Japan

[21] Appl. No.: 339,636

[22] Filed: Jan. 15, 1982

[30] Foreign Application Priority Data

Feb. 5, 1981 [JP] Japan .................................. 56-16172

[51] Int. Cl.³ .......................... A61K 7/06; A61K 7/09; A61K 7/11
[52] U.S. Cl. ......................................... 424/70; 424/47; 424/71; 424/72; 424/359; 424/362
[58] Field of Search ...................... 424/70, 71, 359, 72, 424/47

[56] References Cited

U.S. PATENT DOCUMENTS

| | | | |
|---|---|---|---|
| 3,033,755 | 5/1962 | Jacobi | 424/59 X |
| 3,904,748 | 9/1975 | Eckert et al. | 424/70 |
| 3,957,065 | 5/1976 | Busch et al. | 132/7 |
| 4,041,150 | 8/1977 | Karjala | 424/71 |
| 4,185,087 | 1/1980 | Morlino | 424/70 |
| 4,186,188 | 1/1980 | Gumprecht | 424/70 |
| 4,279,996 | 7/1981 | Yoshioka et al. | 435/69 |
| 4,283,386 | 8/1981 | Van Scott | 424/70 |
| 4,342,742 | 8/1982 | Sebag et al. | 424/70 |

FOREIGN PATENT DOCUMENTS

| | | | |
|---|---|---|---|
| 2600514 | 7/1976 | Fed. Rep. of Germany | 424/71 |
| 2940220 | 4/1980 | Fed. Rep. of Germany | 424/71 |
| 22643 | of 1907 | United Kingdom | 424/70 |
| 1111934 | 5/1968 | United Kingdom | 424/70 |
| 2061956 | 5/1981 | United Kingdom | 424/70 |

*Primary Examiner*—Dale R. Ore
*Attorney, Agent, or Firm*—Oblon, Fisher, Spivak, McClelland & Maier

[57] ABSTRACT

Hair treatments comprising defined amounts of two ingredients, one of which being at least one decomposition derivative of keratin material such as hydrolysates of keratin material alkali salts of decomposition products obtained by oxidation of keratin material and alkali salts of derivatives at the thiol group of decomposition products obtained by reduction of keratin material. The other is at least one silicone derivative of the specific type.

12 Claims, No Drawings

HAIR TREATMENTS

BACKGROUND OF THE INVENTION

1. Field of the Invention

This invention relates to hair treatments which comprise specific types of decomposition derivatives of keratin material and silicone derivatives and exhibit an excellent hair-protecting effect.

2. Description of the Prior Art

Various treatments have ordinarily been applied to hair for beauty care, which will cause the hair to be damaged. For instance, the beauty treatments such as drying with dryer, cold perm, hair dye, hair bleach and the like serve to chemically and physically damage the hair due to the elution of proteins, so that the strength of hair is lowered or the flexibility is lost, causing split ends and broken hairs.

In order to prevent the hair from being damaged, it is the usual practice to use hair rinses and hair treatments which contain quaternary ammonium salts. This practice is certainly effective in softening the hair and preventing the hair from being statically charged but proteins which have once been lost from the hair are not restructured and thus only a transient effect is expected.

SUMMARY OF THE INVENTION

It is accordingly an object of the present invention to provide hair treatments which exhibit the excellent hair-protecting effect.

It is another object of the invention to provide hair treatments which comprise two kinds of ingredients including decomposition derivatives of keratin material and silicone derivatives in which the decomposition derivatives serve to make up for proteins of the hair lost as the result of beauty treatments conducted thereon and silicone derivatives act to prevent the decomposition derivatives from escaping.

It is a further object of the invention to provide hair treatments which can supply proteins of the hair which would be lost during the course of various treatments on the hair.

The above objects can be achieved, according to the invention, by a hair treatment which comprises the following two ingredients (A) and (B):

(A) 0.05–10 wt% of at least one decomposition derivative of keratin material selected from the group consisting of (1) hydrolysates of keratin material, (2) alkali salts of decomposition products obtained by oxidation of keratin material and (3) alkali salts of derivatives at the thiol group of decomposition products obtained by reduction of keratin material; and (B) 0.1–30 wt% of at least one silicone derivatives selected from the group consisting of dimethylpolysiloxanes, methylphenylpolysiloxanes, polyether-modified silicone oils, epoxy-modified silicone oils, fluorine-modified silicone oils, alcohol-modified silicone oils and alkyl-modified silicone oils.

DETAILED DESCRIPTION AND EMBODIMENTS OF THE INVENTION

The decomposition derivatives of keratin material to be the (A) component of the invention can be prepared any of the methods including a method of hydrolyzing keratin material, a method of decomposing keratin material by oxidation and converting the decomposition product into an alkali salt, and a method in which keratin material is decomposed by reduction, chemically modified at the thiol groups of the decomposition product to give a derivative which is then converted into an alkali salt.

The starting keratin materials include, for example, animal hairs, human hair, feathers, hooves, horns, scales and the like. Of these, wool, human hair and feathers are preferably used. These keratin materials may be subjected to the oxidation or reduction reaction as they are but if necessary, they may be cut or reduced into pieces having a suitable size or subjected to pretreatments such as washing and defatting.

The decomposition of the keratin materials is conducted by any of the following methods.

(1) Hydrolysis Reaction (1) Hydrolysis with Acid

Mentioned as acid are, for example, inorganic acids such as hydrochloric acid, sulfuric acid, phosphoric acid, nitric acid, hydrobromic acid and the like, and organic acids such as acetic acid, formic acid, oxalic acid and the like. These acids are generally employed at a concentration of 3–85% and it is desirable that the hydrolysis reaction is invariably caused to proceed at a pH below 4. The reaction temperature is preferably in the range of 40°–100° C. though it may be raised up to 160° C. under pressure. The reaction time is conveniently in the range of 2–24 hours. The reaction product may be used as it is after neutralization with alkalis such as sodium hydroxide, sodium carbonate, ammonia and the like or may be used after subsequent purification such as by gel filtration and ion exchange resins.

The products obtained by the hydrolysis with acid merely undergo the hydrolysis at the polypeptide chains of keratin without involving any other changes, so that they show better results than products obtained by hydrolysis with alkali.

(2) Hydrolysis with Alkali

As alkalis there are used inorganic alkalis such as sodium hydroxide, potassium hydroxide, lithium hydroxide, barium hydroxide, sodium carbonate, potassium carbonate, lithium carbonate, sodium silicate, borax and the like. These alkalis are ordinarily used at a concentration of 1–20%. Larger amounts than as required are unfavorable since the hue of the hydrolysate solution becomes brown or black. The reaction is preferably conducted at a temperature of room temperature to 100° C. for a time of 30 minutes to 24 hours. Care should be taken not to make the temperature higher and the reaction time longer than as required. As the hydrolysis reaction with alkali proceeds, the hydrolysate of keratin is allowed to dissolve out with the attendant advantage that how far the reaction proceeds can visibly be observed. The reaction is completed at the time when the reaction mixture has turned into a uniform solution.

(3) Hydrolysis with Enzyme

Examples of enzymes include acidic proteinases such as pepsin, protease A, protease B and the like, and neutral proteinases such as papain, promeline, thermolycin, trypsin, pronase, chymotrypsin and the like. The pH at the time of the hydrolysis should preferably be controlled to be in the range of 1–3 for the acidic proteinases such as pepsin and in the range of 5–8 for the neutral proteinases such as papain. It is convenient that the pH is properly adjusted by the use of an ammonium acetate/ammonia buffer solution, a phosphate buffer solution and the like buffer solutions. The reaction temperature is favorably in the range of 30°-45° C. and the reaction time is ordinarily in the range of 3-24 hours.

In the hydrolysis reaction with enzymes, the molecular weight of hydrolysate is greatly influenced by the amount of enzyme, the reaction temperature and the reaction time. Accordingly, in order to obtain a keratin hydrolysate with an intended molecular weight, it is necessary to check by the gel filtration technique a distribution of the molecular weight of hydrolysate in relation to variations in the amount of enzyme, reaction temperature and reaction time so as to empirically determine the optimum conditions.

The hydrolysates obtained from enzymes show a narrower distribution of molecular weight tha hydrolysates obtained from acids or alkalis and contain reduced amounts of free amino acids, thus being more favorable for use as cosmetics.

The hydrolysates obtained by these hydrolysis reactions should preferably have an average molecular weight of from 200 to 5,000. This is because the adsorptivity of the decomposition products of keratin on hair depends on the molecular weight of the products and a product with a molecular weight of about 1,000 is most ready to adsorb on hair but those having average molecular weights larger than 5,000 scarcely adsorb on hair. The disulfide bonds in the keratin decomposition derivatives should preferably be left in amounts as large as possible. To this end, it is needed to use a keratin material of high purity and to effect the hydrolysis reaction under mild conditions.

(2) Oxidation and Decomposition Reaction

The oxidation of keratin material is feasible by any of methods known per se (N. H. Leon; Textile progress, Vol. 7, page 1 (1975)). Oxidizing agents are preferably of the type which may be either organic or inorganic but acts electrophilically on the disulfide bonds (S-S bonds) in the keratin structure. Examples of the oxidizing agents include organic peracids, inorganic peroxo acids or their salts, permanganic acid or its salts, chromic acid or related compounds, halogens, peroxides, oxyacids or their salts and the like, among which the organic peracids such as peracetic acid, performic acid and perbenzoic acid are most preferable.

The oxidation reaction is conducted in liquid media using oxidizing agents in excess with respect to the disulfide bonds in keratin material, ordinarily in amounts of over two equivalents or more, preferably 4-10 equivalents, of the sulfide bonds. The reaction may be carried out acidic or alkaline conditions and is preferably conducted under acidic and particularly weakly acidic conditions. The conditions such as reaction temperature and pressure vary depending on the types of the oxidizing agent and keratin material and are not critical. In general, the reaction temperature is room temperature but, if necessary, heat may be applied. The pressure is a normal pressure but the reaction may be conducted under reduced pressure or under pressure.

By this, the disulfide bonds of keratin material are cleft into sulfonic acid (—SO₃H).

(3) Reduction Reaction and Chemical Modification Reaction

Reducing agents employed for reducing keratin materials are preferably organic or inorganic reducing agents of the type which can serve to cleave the disulfide bond in the keratin structure into a thiol group (—SH) and generally act nucleophilically on the disulfide bonds. Examples of the reducing agents include organic reducing agents such as mercaptoethanol, thioglycollic acid, benzylmercaptan, 1,4-dithiothreitol, tributylphosphine and the like and inorganic reducing agents such as sodium hydrogensulfite, sulfides such as sodium hydrogensulfide, methallic hydrides such as lithium aluminium hydride.

The amount of the reducing agent is usually in the range of 2-10 equivalents of the disulfide bonds in keratin material. The pH of the reaction system is in the range of 2-12, preferably 6-11. Outside the range, the hydrolysis undesirably takes place at the same time. The reaction temperature is sufficiently room temperature but heat may be applied to shorten the reaction time. The reaction time is normally in the range of 2-3 hours or more. Since it is necessary that the thiol groups produced by the reaction do not substantially undergo oxidation, the reduction operation should favorably be carried out in an atmosphere of inret gas to give good results.

The decomposition product obtained by the reduction of keratin material is then chemically modified at the thiol groups thereof to obtain a derivative thereof (hereinafter referred to as keratin material reductions derivative). The derivatives at the thiol group include:

—SCH₂COOH, —SCH₂CH₂COOH, —SCHCOOH,
                                                                             CH₂COOH

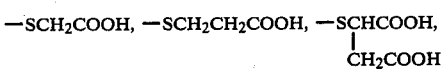

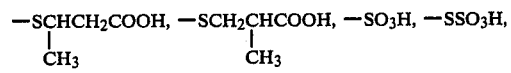

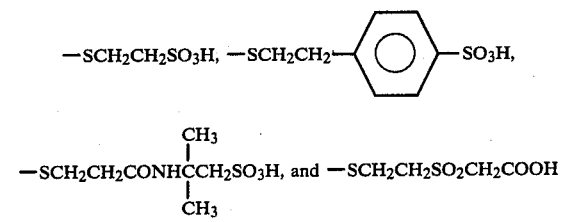

among which —SCH₂COOH, —SCHCOOH are preferable.
                                                              CH₂COOH The chemical modification of thiol group is known per se and can be conducted, for example, on the basis of procedures known from N. H. Leon; Textile Progress, Vol. 7 (1975), "Yuki Ioo Kagobutsu (Organic Sulfur Compounds)" written by Shigeru Ookyo and published by Kagaku Dojin (1968) and "Kobunshi Jikkengaku Koza" written by Masami Oku, Vol. 12, Kyoritsu Shuppan (1957). Typical methods are as follows.

(1) Method utilizing the nucleophilic substitution reaction of SH group

(in which K represents a residue of keratin material, R represents a chemically modifying group to be introduced, and L represents leaving atom or group such as a halogen atom or an acid residue). Compounds reacting by this method include, for example, halogen compounds such as iodoacetic acid, bromoacetic acid, chloroacetic acid and the like.

(2) Method utilizing the nucleophilic addition reaction of SH group with a double bond existing between carbon atoms

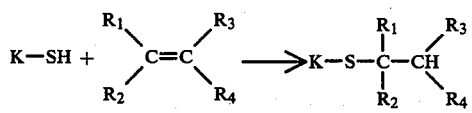

(in which at least one of $R_1$, $R_2$, $R_3$ and $R_4$ represents a group having a carboxyl group or sulfonic acid group therein and the other independently represent an alkyl group or hydrogen atom, and K has the same meaning as defined hereinbefore).

Compounds reacting with the K-SH by this method include, for example, acrylic acid, methacrylic acid, crotonic acid, maleic acid, fumaric acid, vinyl carboxymethylsulfone, vinyl sulfonic acid, vinylsulfonic acid, styrenesulfonic acid, 2-acrylamido-2-methylpropanesulfonic acid and the like.

(3) Method using a substitution reaction between SH group and sulfite compound

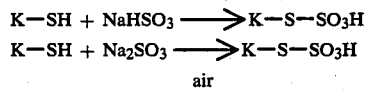

(in which K has the same meaning as defined hereinbefore).

(4) Method of oxidizing SH group into sulfonic acid group

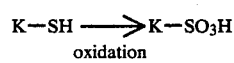

(in which K has the same meaning as defined hereinbefore).

The oxidizing agents used in this reaction include, for example, halogens, permanganates and the like.

Alkali salts of the decomposition product obtained by oxidation of keratin material and reduction derivatives of keratin material include salts with inorganic alkali metals such as sodium, potassium, and the like, ammonium salts, and salts with organic bases such as ethanolamine, diethanolamine, triethanolamine, 2-amino-2-methylpropanol, aminomercaptopropanediol, triisopropanolamine, glycine, histidine, arginine and the like. These salts may be prepared separately and then added to hair treatments. Alternatively, the oxidation decomposition product of keratin material or the reduction derivative of keratin material and alkaline materials may be added to hair treatments in which they are converted into a salt thereof. Examples of the alkaline materials include sodium inorganic alkaline materials such as sodium hydroxide, potassium hydroxide, sodium carbonate, potassium carbonate and the like, ammonia, organic alkaline materials such as ethanolamine, diethanolamine, triethanolamine, amino-2-methyl-1-propanol, 2-amino-2-methyl-1,3-propanediol, 2-amino-2-methyl-1-propanol, 2-amino-2-ethyl-1,3-propanediol, 2-amino-1-butanol, triisopapanolamine, diisopropanolamine, monoisopropanolamine, lysine, arginine, histidine, hydroxylysine and the like. These alkaline materials are preferably added in an amount of 0.1-8 equivalents of the carboxyl groups or sulfonic acid groups in the oxidation decomposition product or reduction derivative of keratin material.

At least one of the thus obtained (A) components is added to a hair treatment in an amount of 0.05-10.0 wt% (hereinafter referred to simply as %), preferably 0.1-1.0% of the composition.

Preferable silicone derivatives to be the (B) component of the invention are shown below.

(1) Dimethylpolysiloxanes of the following formula (II)

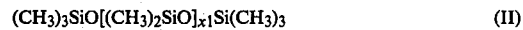

(in which x1 is an integer of 3-650).

(2) Methylphenylpolysiloxanes of the following formula (III) or (IV)

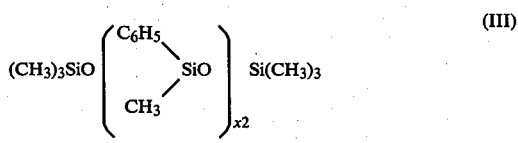

(in which x2 represents an integer of 1-500, and the sum of x3 and y3 is an integer of 1-500).

(3) Polyether-modified silicone oils of the following formula (V)

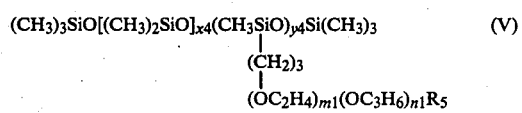

(in which $R_5$ represents an alkyl group having 1-12 carbon atoms, an alkoxy group having 1-6 carbon atoms or a hydroxyl group, x4 is an integer of 1-100, preferably 20-30, y4 is an integer of 1-20, preferably 2-10, m1 is an integer of 0-50, preferably 20-30, and n1 is an integer of 0-50, preferably 20-30).

(4) Epoxy-modified silicone oils of the following formula (VI)

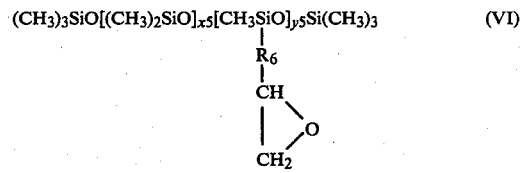

(in which $R_6$ represents an alkylene group having 1-3 carbon atoms, x5 is an integer of 1-500, preferably 1-250, and y5 is an integer of 1-50, preferably 1-30).

(5) Fluorine-modified silicone oils of the following formula (VII)

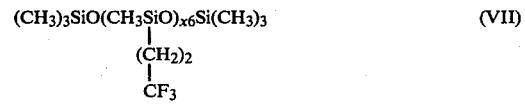

(in which x6 is an integer of 1-400, preferably 1-250).

(6) Alcohol-modified silicone oils of the following formula (VIII) or (IX)

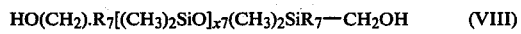

-continued

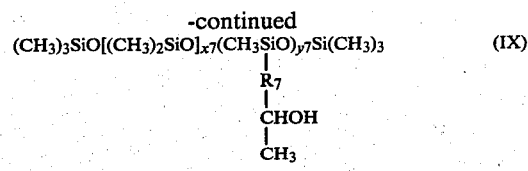

(in which $R_7$ is absent or an alkylene group having 1-4 carbon atoms, and x7 and y7 are independently an integer of 1-500, preferably 1-200).

(7) Alkyl-modified silicone oils of the following formula (X) or (XI)

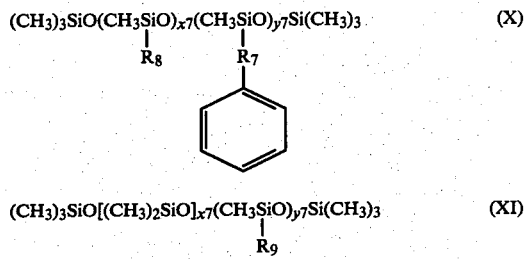

(in which $R_8$ represents an alkyl group having 2-18 carbon atoms, $R_9$ represents an alkyl group having 10-16 carbon atoms, and $R_7$, x7 and y7 have the same meanings as defined above).

The silicone derivatives of the formulas (1)-(7) may be used singly or in combination, among which in view of imparting good touch to the treated hair, polyether-modified silicone oils, dimethylpolysiloxanes and methylphenylpolysiloxanes are preferable.

These (B) components are, as described hereinbefore, added in an amount of 0.1-30%, preferably 1.0-5.0% of the treatment composition.

The hair treatment according to the invention can be prepared either by dissolving the (A) and (B) components in suitable solvent as usual, or by mixing them with surface active agents to use in the form of an emulsion, suspension or gel. Examples of the solvent include, for example, water, lower alcohols having 1-3 carbon atoms, propylene glycol, glycerine and the like.

As a matter of course, to the hair treatment according to the invention may be further added arbitrary ingredients depending on the end use within ranges whereby the effect of the hair treatment is not impeded. Examples of such ingredients include surface active agents such as anionic surface active agents, cationic surface active agents, nonionic surface active agents and amphoteric surface active agents, oil such as fatty higher alcohols, lanolin oil, esters, liquid paraffin and the like, thickness such as hydroxyethyl cellulose, methyl cellulose, hydroxypropylmethyl cellulose and the like, preservatives, perfumes and the like.

The thus obtained hair treatment can be in the form of an aqueous emulsion, ethanol solution, emulsion, suspension or gel. In other words, the hair treatment can be used in any known forms including shampoo, hair rinse, hair treatment, pre-shampoo, hair spray, hair brushing lotion, hair setting lotion, hair liquid, hair tonic and the like.

The present invention is particularly described by way of synthetic examples and examples, which should not be construed as limiting the present invention thereto.

SYNTHETIC EXAMPLE 1

Preparation of Decomposition Derivatives by Oxidation of Keratin Material:

(a) Ten grams of wool fibers were immersed in 700 g of an aqueous 8% peracetic acid solution at room temperature for 1 day to conduct an oxidation reaction. The resulting oxidized wool fibers were filtered, washed with water and immersed in 700 g of a 0.1 N ammoniacal solution at room temperature for 1 day, permitting about 90% of the wool to dissolve in the ammoniacal solution. About 1 g of the insoluble matters were removed by filtration and the aqueous ammoniacal solution of keratose to be an oxidized decomposition product of the wool keratin was admixed with 2 N hydrochloric acid to have its pH of 4.0, whereupon α-keratose was settled as a precipitate. This precipitate was filtered, washed with acetone and dried to obtain 5.4 g of α-keratose.

(b) Wool fibers were heated under pressure in an autoclave by the use of saturated steam of 6 kg/cm² for 6 minutes and were abruptly released in the air to obtain a porous puffed product. Ten grams of the puffed product which had been reduced into pieces, 250 g of formic acid and 50 g of a 30% aqueous hydrogen peroxide solution were charged into a 500 ml three neck distillation flast to immerse the pieces at room temperature for 1 day, whereupon no powder was found in the solution but foam-like masses were floated in the upper layer. This reaction mixture was filtered and the filtrate was poured into 1.5 l of water, followed by adding hydrochloric acid to adjust the pH to 4. The resulting precipitate was collected by filtration and washed with 500 ml of water to obtain 4.5 g of α-keratose. To the insoluble matter from which the reaction product had been removed by filtration were added 350 ml of water and then an ammoniacal solution to adjust the pH to 11, allowing the matter to be immersed at room temperature for 1 day. The system was filtered and hydrochloric acid was added to the filtrate to adjust the pH to 4. The resulting precipitate was collected by filtration to obtain 0.7 g of α-keratose. It was found that 1.4 g of the insoluble matters were primarily made of β-keratose.

SYNTHETIC EXAMPLE 2

Preparation of Reduced Decomposition Derivatives of Keratin Materials:

(a) Ten grams of wool fibers were immersed in 600 ml if an aqueous solution with concentrations of 8 M urea and 0.01 M Tris buffer, to which was added 6 ml of 2-mercaptoethanol, followed by adjusting the pH to 10 by means of a 5 N potassium hydroxide aqueous solution to conduct the reduction reaction in a stream of nitrogen at room temperature. About 3 hours after commencement of the reaction, the wool dissolved in the reaction solution in an amount of about 85% thereof. While the system was adjusted with a 5 N potassium hydroxide solution so that the pH was not below 7, 16.5 g of iodoacetic acid was gradually added and the pH of the system was adjusted finally to 8.5 to carry out the carboxymethylation reaction at room temperature for 2 hours. The reaction solution was filtered to remove insoluble matters therefrom and the resultant filtrate was charged into a cellulose tube wherein it was dialyzed against ion-exchanged water to remove low molecular weight impurities including urea. As the urea was dialyzed, the content in the cellulose tube became white since HGT (components with high contents of glycine and tyrosine) to be water-insoluble components was caused to precipitate. After completion of the dialysis, the HGT was centrifugally removed and S-carboxymethyl keratin (SCMKA) was obtained from the neutral transparent solution of SCMKA by the isoelectric precipitation method. That is, 1 N hydrochloric acid was added to the system to adjust its pH to 4.4 by which SCMKA became insoluble and separated as precipitate. This precipitate was filtered, washed with ethanol and dried to obtain 4.2 g of SCMKA.

(b) The procedure of Synthetic Example 2(a) was repeated except that there was used instead of wool fibers feathers which were heated for 6 minutes in an autoclave by means of a superheated steam of 6 kg/cm$^2$ and 240° C. and then abruptly released in the air to obtain a porous puffed product and that 1.75 g of maleic acid was used instead of iodoacetic acid, thereby obtaining 5.3 g of S-(1,2-dicarboxy-ethyl)-keratin.

(c) The procedure of Synthetic Example 2(a) was repeated using a powder of hoof of horse instead of wool fibers and 11 g of acrylic acid instead of iodoacetic acid, thereby obtaining 4.2 g of S-(2-carboxyethyl)-keratin.

(d) The procedure of Synthetic Example 2(a) was repeated using 28 g of styrenesulfonic acid instead of iodoacetic acid thereby obtaining 4.8 g of S-(sulfophenylvinyl)-keratin.

(e) Eight grams of wool fibers were dispersed in 300 ml of n-propanol and 300 ml of a 0.1 N tris buffer solution. After substitution with nitrogen, 3,2 ml of tri-n-butylphosphine was added, followed by agitating at room temperature for 24 hours. The solution was subjected to filtration and to the resulting insoluble matters were added 400 ml of water, 9.28 g of maleic acid and about 30 ml of 5 N potassium hydroxide to adjust the pH to 8.0, followed by agitating at room temperature for 6 hours. To the reaction system was added about 20 ml of a 28% aqueous ammoniacal solution to adjust the pH to 11.5, after which it was agitated at room temperature for 18 hours. The reaction solution was filtered to remove insoluble matters therefrom and the resultant filtrate was placed in a cellulose tube in which it was dialyzed against ion-exchanged water to remove low molecular weight impurities therefrom. After completion of the dialysis, the insoluble matters in the cellulose tube were removed by centrifugal separation and the resulting neutral transparent aqueous solution was adjusted in pH to 4.4 by addition of about 5.5 ml of 1 N hydrochloric acid and the resulting precipitate was collected by filtration, washed with ethanol and dried to obtain 3.9 g of S-(1,2-dicarboxyethyl)-keratin.

(f) The procedure of Synthetic Example 2(e) was repeated except that there was used instead of wool fibers a powder of a porous puffed product which had been obtained by heating wool in an autoclave by means of saturated steam of 6 kg/cm$^2$ for 6 minutes and releasing the heated wool in the air abruptly and that 16.5 g of 2-acrylamido-2-methylpropanesulfonic acid instead of maleic acid, thereby obtaining 4.5 g of keratin-S-(2-acrylamido-2-methylpropanesulfonic acid).

SYNTHETIC EXAMPLE 3

Preparation of Hydrolysis Derivatives of Keratin Materials:

(a) Ten grams of wool fibers were immersed in 300 g of a 1% sodium hydrogensulfite aqueous solution, whose pH was adjusted to 6.7 by means of a 5 N aqueous caustic soda solution. Thereafter, 0.2 g of papain was added to the system to conduct the hydrolysis reaction at 60° C. for 15 hours, by which about 80% of the wool dissolved. Insoluble matters were removed by filtration and the sulfite contained in the resulting filtrate was removed by an ultrafiltration technique using a membrane with a fractional molecular weight of 500. The aqueous solution of the hydrolysate was concentrated and freeze dried to obtain 7.7 g of the hydrolysate having a molecular weight of 500–2000.

(b) Ten grams of wool fibers were immersed in 300 g of a 75% phosphoric acid aqueous solution and the hydrolysis reaction was conducted at 120°–130° C. for 5 hours. The reaction system was cooled and filtered to remove insoluble matters therefrom, to which was added water of 4–5 times in volume of the filtrate to further remove insoluble matters. Then, calcium carbonate or barium hydroxide was added to the filtrate to adjust its pH to 6.7, after which the resulting precipitate was collected by filtration and dried to obtain 8.0 g of a hydrolysate having a molecular weight of 500–2000.

Note: The amount of S—S bonds in the hydrolysate obtained by the procedure of Synthetic Example 3(a) or 3(b) was 50 moles per $10^5$ g of the hydrolysate, revealing that little or no cystine in the wool was destroyed during the course of the hydrolysis.

(c) One hundred grams of feathers were heated under pressure in an autoclave for 6 minutes by the use of superheated steam of 6 kg/cm$^2$ and 240° C. and then abruptly released in the air to obtain a porous puffed product. This product was reduced into pieces, to which was added 3 l of 0.3 N caustic soda for conducting the hydrolysis reaction at 60° C. for 18 hours, followed by neutralizing with 1 N hydrochloric acid and filtering the reaction solution. The sodium chloride in the resulting filtrate was removed by the ultrafiltration method using a membrane with a fractional molecular weight of 500. The aqueous solution of the hydrolysate of the keratin was concentrated and free dried to obtain 7.2 g of the hydrolysate of the keratin. The molecular weight of the hydrolysate was found to be 1,800 when determined by the gel filtration method.

(d) 100 g of pieces of horse's hoof with a uniform size of 0.25–1 mm were defatted with a 50% methanol and 50% chloroform solution and then treated with a 1% ammoniacal solution to remove soluble proteins therefrom, which was then placed in a three neck flask, followed by adding 20 g of sodium hydroxide and 400 g of ion-exchanged water and subjecting to the hydrolysis reaction at 90° C. for 4 hours while agitating. After cooling, hydrochloric acid was added to adjust the pH to 8 and the reaction solution was filtered. The sodium chloride in the filtrate was removed, followed by repeating the procedure of Synthetic Example 3(c) to obtain 68 g of a hydrolysate of the keratin. This hydrolysate had a molecular weight of 2,500 when measured by the gel filtration method.

EXAMPLE 1

Hair treatments of the following compositions were prepared and their hair-protecting effect was checked. The hair protecting effect was determined as follows: 5 g of each hair treatment was dispersed in 500 ml of ion-exchanged water, in which a tress of hairs having a length of 20 cm and a weight of 5 g were immersed for 5 minutes, then rinsed with running water for 5 minutes, dried and combed with a nylon brush 500 times to measure a weight of broken hairs collected during the combing.

| Formulation | |
|---|---|
| Decomposition derivatives of keratin materials (Table 1) | 1.0% |
| Silicone derivatives (Table 1) | 3.0 |
| Alkaline Materials or surface active agents (Table 1) | 2.0 |
| Water | balance |
| pH | (7.0) |

Preparation:

Decomposition derivatives of keratin materials and silicone derivatives were added to water, to which surface active agents were added while agitating and then the pH of each composition was adjusted to 7.0 by addition of an alkaline material.

TABLE 1

| | Decomposition Derivatives of Keratin Materials | Silicone Derivatives | Alkaline Materials or Surface Active Agents | Weight of Broken Hairs (%) |
|---|---|---|---|---|
| Inventive Products | Synthetic Example 1(a) | General formula (II) | — | 0.091 |
| | Synthetic Example 1(a) | General formula (V) | — | 0.105 |
| | Synthetic Example 1(a) | General formula (VII) | — | 0.077 |
| | Synthetic Example 2(e) | General formula (III) | — | 0.071 |
| | Synthetic Example 2(e) | General formula (VII) | — | 0.065 |
| | Synthetic Example 3(a) | General formula (II) | — | 0.051 |
| | Synthetic Example 3(a) | General formula (VI) | — | 0.044 |
| | Synthetic Example 1(a) | General formula (II) | Sodium laurylsulfate | 0.071 |
| | Synthetic Example 1(a) | General formula (V) | " | 0.096 |
| | Synthetic Example 2(b) | General formula (II) | " | 0.121 |
| | Synthetic Example 2(b) | General formula (IV) | " | 0.099 |
| | Synthetic Example 3(a) | General formula (II) | " | 0.109 |
| | Synthetic Example 3(a) | General formula (V) | " | 0.131 |
| | Synthetic Example 1(a) | General formula (II) | Cetyltrimethylammonium chloride | 0.006 |
| | Synthetic Example 1(a) | General formula (IV) | " | 0.009 |
| | Synthetic Example 2(e) | General formula (IV) | " | 0.071 |
| | Synthetic Example 2(e) | General formula (V) | " | 0.086 |
| | Synthetic Example 3(b) | General formula (II) | " | 0.081 |
| | Synthetic Example 3(b) | General formula (IV) | " | 0.009 |
| | Synthetic Example 1(a) | General formula (IV) | polyoxyethylene(15) stearyl ether | 0.121 |
| | Synthetic Example 1(a) | General formula (V) | " | 0.171 |
| | Synthetic Example 2(b) | General formula (IV) | " | 0.098 |
| | Synthetic Example 2(b) | General formula (II) | " | 0.200 |
| | Synthetic Example 3(a) | General formula (IV) | " | 0.173 |
| | Synthetic Example 3(a) | General formula (II) | " | 0.133 |
| | Synthetic Example 3(b) | General formula (V) | " | 0.147 |
| | Synthetic Example 3(b) | General formula (II) | " | 0.111 |
| | | | formula (IV) | |
| Comparative Products | — | — | sodium laurylsulfate | 0.726 |
| | — | — | cetyltrimethylammonium chloride | 0.431 |
| | — | — | polyoxyethylene(15) stearyl ether | 0.861 |
| | Synthetic Example 1(a) | — | — | 0.136 |
| | Synthetic Example 2(b) | — | — | 0.261 |
| | Synthetic Example 2(e) | — | — | 0.333 |
| | Synthetic Example 3(a) | — | — | 0.179 |

TABLE 1-continued

| Decomposition Derivatives of Keratin Materials | Silicone Derivatives | Alkaline Materials or Surface Active Agents | Weight of Broken Hairs (%) |
|---|---|---|---|
| Synthetic Example 3(b) | — | — | 0.269 |
| — | General formula (II) | — | 0.371 |
| — | General formula (IV) | — | 0.369 |
| — | General formula (V) | — | 0.451 |

The silicone derivatives indicated in Table 1 have the following values in the respective general formulas.

Formula
(II) $x_1 = 200$
(III) $x_2 = 100$
(V) $R_5 = C_4$, $x_4 = 25$, $y_4 = 10$, $m_1 = n_1 = 20$
(VI) $R_6 = C_1$, $x_5 = 200$, $y_5 = 20$
(VII) $x_6 = 220$
(VIII) $R_7 = C_1$, $x_7 = y_7 = 200$ From the results of Table 1, it will become apparent that the inventive products are more excellent in hair-protecting effect than the comparative products.

EXAMPLE 2

| | Shampoo Composition (Formulation) | |
|---|---|---|
| A | triethanolamine laurylsulfate | 15.0(%) |
| B | diethanolamine laurate | 5.0 |
| C | hydroxyethyl cellulose | 0.5 |
| D | ethanol | 3.0 |
| E | decomposition derivative of keratin material (Synthetic Example 2(b)) | 2.0 |
| F | silicone derivative ($x_3 = y_3 = 200$ in general formula (IV)) | 3.0 |
| G | water | balance |
| H | triethanolamine | amount sufficient for pH = 7.0 |

(Preparation)

E was added to G, to which H was added so that the pH was 7.0 thereby causing E to dissolve. Then, A, B, C, D and F were added, followed by heating to 70° C. After uniform dissolution of all the components, the mixture was cooled to obtain a shampoo composition.

EXAMPLE 3

| | Hair Rinse (Formulation) | |
|---|---|---|
| A | distearyldimethylammonium chloride | 1.0(%) |
| B | cetyl alcohol | 2.0 |
| C | decomposition derivative of keratin material (Synthetic Example 3(a)) | 2.0 |
| D | silicone derivative (of general formula (II) wherein $x_1 = 200$) | 3.0 |
| E | water | balance |
| F | NaOH aqueous solution (1N) | amount sufficient for pH = 7.0 |

(Preparation)

C was dispersed in E and heated to 70° C., to which a solution of a mixture of A, B and D of the same temperature was added and agitated. After cooling to 45° C., the pH of the mixture was adjusted by F to obtain a hair rinse.

EXAMPLE 4

| | Hair Conditioner (Formulation) | |
|---|---|---|
| A | decomposition derivative of keratin material (Synthetic Example 2(a)) | 1.0(%) |
| B | silicone derivative of the formula (V) wherein $R_5 = c_4$, $x_4 = 25$, $y_4 = 10$, $m_1 = n_1 = 20$) | 3.0 |
| C | methylparaben | 0.1 |
| D | ethanol | 10.0 |
| E | water | balance |
| F | arginine | amount sufficient for pH = 7.0 |

(Preparation)

To E were added A, B, C and D, to which was added F while agitating to adjust the pH to 7.0, thereby obtaining a hair conditioner.

EXAMPLE 5

| | Two-phase Hair Setting Lotion (Formulation) | |
|---|---|---|
| A | decomposition derivative of keratin (Synthetic Example 1(a)) | 1.0(%) |
| B | silicone derivative (of the general formula (II) in which $x_1 = 250$) | 15.0 |
| C | ethanol | 10.0 |
| D | hydroxyethyl cellulose | 0.5 |
| E | water | balance |
| F | triethanolamine | amount sufficient for pH = 7.0 |

(Preparation)

To E were added A, C and D, whose pH was adjusted to 7.0 by means of F, to which B was added to give a two-phase hair setting lotion.

EXAMPLE 6

| | Hair Liquid (Formulation) | |
|---|---|---|
| A | decomposition derivative of keratin (Synthetic Example 3(a)) | 0.5(%) |
| B | silicone derivative (Same as used in Example 4) | 3.0 |
| C | polyoxypropylene (30) butyl ether | 15.0 |
| D | ethanol | 40.0 |
| E | water | balance |
| F | triethanolamine | amount sufficient |

-continued

| Hair Liquid | |
|---|---|
| (Formulation) | |
| | for pH = 7.0 |

(Preparation)

A–E were mixed, to which F was added to adjust the pH to 7.0, followed by completely dissolving all the components to obtain a hair liquid.

EXAMPLE 7

| | Hair Tonic | |
|---|---|---|
| | (Formulation) | |
| A | decomposition derivative of keratin (Synthetic Example 3(a)) | 0.5(%) |
| B | silicone derivative (of the general formula (V) in which $R_5 = c_2$, $x_4 = 10$, $m_1 = n_1 = 20$) | 5.0 |
| C | PCA - Al | 0.5 |
| D | ethanol | 55.0 |
| E | water | balance |
| F | arginine | amount sufficient for pH = 7.5 |

(Preparation)

A and C were dissolved in E, to which a solution of B in D was added to give a hair tonic.

EXAMPLE 8

| | Hair Brushing Lotion | |
|---|---|---|
| | (Formulation) | |
| A | decomposition derivative of keratin (Synthetic Example 2(b)) | 2.0(%) |
| B | silicone derivative (of the general formula (IV) in which $x_3 = y_3 = 200$) | 2.0 |
| C | ethanol | 10.0 |
| D | polyethylene glycol 6000 | 5.0 |
| E | water | balance |
| F | arginine | amount sufficient for pH = 6.5 |

(Preparation)

A–D were dispersed in E, whose pH was adjusted to 6.5 by the use of arginine and the components were dissolved to give a hair brushing lotion.

What is claimed is:

1. A hair treatment composition selected from the group consisting of shampoo, hair rinse, hair treatment, pre-shampoo, hair spray, hair brushing lotion, hair setting lotion, hair liquid and hair tonic which comprises the following two ingredients (A) and (B):

(A) 0.05–10 wt% of at least one decomposition derivative of keratin material selected from the group consisting of (1) alkali salts of decomposition products obtained by oxidation of keratin material and (2) alkali salts of derivatives in the thiol group of decomposition products obtained by reduction of keratin material; and (B) 0.1–30 wt% of at least one silicone derivative selected from the group consisting of (1) dimethylpolysiloxanes of the formula (II)

$$(CH_3)_3SiO[(CH_3)_2SiO]_{x1}Si(CH_3)_3 \quad (II)$$

in which x1 is an integer of 3–650, (2) methylphenylpolysiloxanes of the formula (III) or (IV)

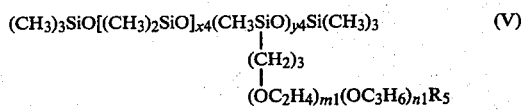

$$(CH_3)_3SiO[(CH_3)_2SiO]_{x3}[(C_6H_5)_2SiO]_{y3}Si(CH_3)_3 \quad (IV)$$

in which x2 is an integer of 1–500, and the sum of x3 and y3 is an integer of 1–500, (3) polyether-modified silicone oils of the formula (V)

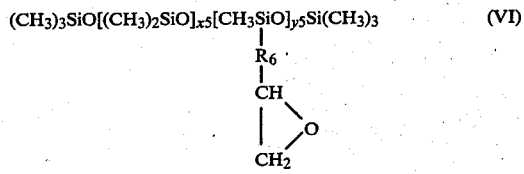

in which $R_5$ represents an alkyl group having 1–12 carbon atoms, an alkoxy group having 1–6 carbon atoms or a hydroxyl group, x4 is an integer of 1–100, y4 is an integer of 1–20, m1 is an integer of 0–50, and n1 is an integer of 0–50, (4) epoxy-modified silicone oils of the formula (VI)

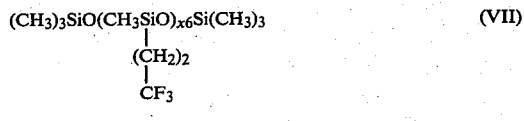

in which $R_6$ represents an alkylene group having 1–3 carbon atoms, x5 is an integer of 1–500, and y5 is an integer of 1–50, (5) fluorine-modified silicone oils of the formula (VII)

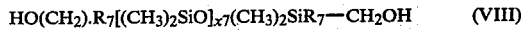

in which x6 is an integer of 1–400, (6) alcohol-modified silicone oils of the formula (VIII) or (IX)

$$HO(CH_2).R_7[(CH_3)_2SiO]_{x7}(CH_3)_2SiR_7-CH_2OH \quad (VIII)$$

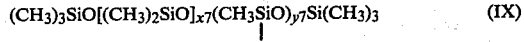

in which $R_7$ is not present or represents an alkylene grouping have 1–4 carbon atoms, and x7 and y7 are independently an integer of 1–500, and (7) alkyl-modified silicone oils of the formula (X) or (XI)

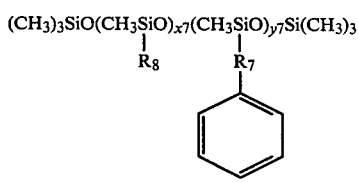
(X)

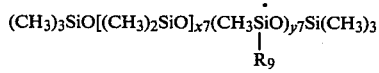
(XI)

in which $R_8$ represents an alkyl group having 2–18 carbon atoms, $R_9$ represents an alkyl group having 10–16 carbon atoms, and $R_7$, x7 and y7 have the same meanings as defined before, respectively, and a solvent.

2. A hair treatment according to claim 1, wherein the solvent is selected from the group consisting of water, lower alcohols having 1–3 carbon atoms, propylene glycol and glycerine.

3. The hair treatment according to claim 1, wherein said dimethylpolysiloxanes are those of the following formula (II)

$$(CH_3)_3SiO[(CH_3)_2SiO]_{x1}Si(CH_3)_3 \quad (II)$$

in which x1 is an integer of 3–650.

4. The hair treatment according to claim 1, wherein said methylphenylpolysiloxanes are those of the following formula (III) or (IV)

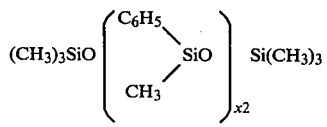
(III)

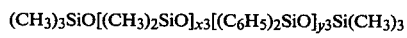
(IV)

in which x2 is an integer of 1–500, and the sum of x3 and y3 is an integer of 1–500.

5. The hair treatment according to claim 1, wherein said polyether-modified silicone oils are those of the following formula (V)

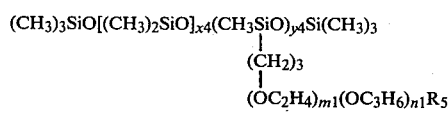
(V)

in which $R_5$ represents an alkyl having 1–12 carbon atoms, an alkoxy group having 1–6 carbon atoms or a hydroxyl group, x4 is an integer of 1–100, y4 is an integer of 1–20, m1 is an integer of 0–50, and n1 is an integer of 0–50.

6. The hair treatment according to claim 1, wherein said epoxy-modified silicone oils are those of the following formula (VI)

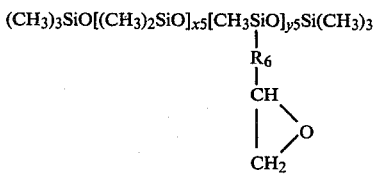
(VI)

in which $R_6$ represents an alkylene group having 1–3 carbon atoms, x5 is an integer of 1–500, and y5 is an integer of 1–50.

7. The hair treatment according to claim 1, wherein said fluorine-modified silicone oils are those of the following formula (VII)

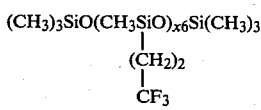
(VII)

in which x6 is an integer of 1–400.

8. The hair treatment according to claim 1, wherein said alcohol-modified silicone oils are those of the following formula (VIII) or (IX)

$$HO(CH_2).R_7[(CH_3)_2SiO]_{x7}(CH_3)_2SiR_7-CH_2OH \quad (VIII)$$

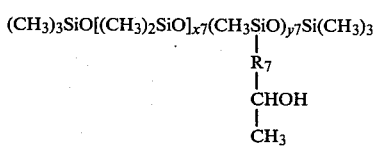
(IX)

in which $R_7$ is not present or represents an alkylene group having 1–4 carbon atoms, and x7 and y7 are independently an integer of 1–500.

9. The hair treatment according to claim 1, wherein said alkyl-modified silicone oils are those of the following formula (X) or (XI)

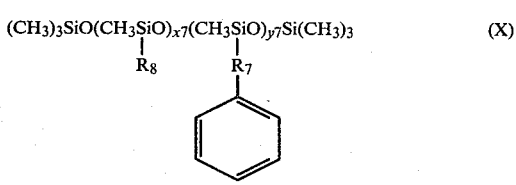
(X)

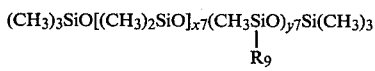
(XI)

in which $R_8$ represents an alkyl group having 2–18 carbon atoms, $R_9$ represents an alkyl group having 10–16 carbon atoms, and $R_7$, x7 and y7 have the same meanings as defined before, respectively.

10. The hair treatment composition according to claim 1, wherein said at least one decomposition derivative is used in an amount of 0.1–10 wt% and said at least one silicone derivative is used in an amount of 1.0–5.0 wt%, both based on the total composition.

11. The hair treatment composition according to claim 1, wherein said composition is in the form of a solution.

12. The hair treatment composition according to claim 1, wherein said composition is in the form of an emulsion, suspension or gel.

* * * * *